United States Patent
Bompeix et al.

(10) Patent No.: US 6,723,364 B1
(45) Date of Patent: Apr. 20, 2004

(54) FOG TREATMENT METHOD USING A LIQUID COMPOSITION FOR TREATING FRUITS AND VEGETABLES AND IMPLEMENTING DEVICE

(75) Inventors: Gilbert Bompeix, Paris (FR); Alberto Sardo, Chateaurenard (FR)

(73) Assignee: Xeda International, Saint-Andiol (FR)

( * ) Notice: Subject to any disclaimer, the term of this patent is extended or adjusted under 35 U.S.C. 154(b) by 0 days.

(21) Appl. No.: 09/601,381

(22) PCT Filed: Dec. 3, 1999

(86) PCT No.: PCT/FR99/03006

§ 371 (c)(1), (2), (4) Date: Oct. 23, 2000

(87) PCT Pub. No.: WO00/32063

PCT Pub. Date: Jun. 8, 2000

(30) Foreign Application Priority Data

Dec. 3, 1998 (FR) ............................................. 98 15305
Apr. 12, 1999 (FR) ............................................. 99 04534

(51) Int. Cl.[7] ................................................. A23L 1/00
(52) U.S. Cl. ....................... 426/320; 426/102; 426/321; 426/335; 426/541; 426/615
(58) Field of Search .......................... 426/89, 102, 320, 426/321, 323, 331, 35, 506, 541, 615, 335

(56) References Cited

U.S. PATENT DOCUMENTS

| | | | |
|---|---|---|---|
| 3,518,096 A | 6/1970 | Layton | ........................ 99/154 |
| 4,857,345 A | 8/1989 | Sardo | ......................... 426/310 |
| 5,679,351 A | 10/1997 | Walter et al. | ............ 424/195.1 |

FOREIGN PATENT DOCUMENTS

| | | |
|---|---|---|
| EP | 0719499 | 7/1996 |
| EP | 0795272 | 9/1997 |
| EP | 0842605 | 5/1998 |
| FR | 2566681 | 1/1986 |
| FR | 2733393 | 10/1996 |
| GB | 641739 | 8/1950 |

*Primary Examiner*—Leslie Wong
(74) *Attorney, Agent, or Firm*—Wenderoth, Lind & Ponack, L.L.P.

(57) ABSTRACT

The invention concerns a fog treatment method using a liquid composition for treating fruits and vegetables, characterised in that it consists in producing a fog treatment mist consisting of droplets having a temperature ranging between 200 and 280° C. and driven at a linear speed ranging between 110 and 140 m/s. More precisely, said method consists in forming said fog treatment mist in the outlet of the cylindrical channel by injecting, at the intake of said channel, said composition into a hot air jet sprayed at high speed into said channel intake, the hot air jet temperature before injection being between 550 and 750° C. and said hot air jet linear speed, before injection, ranging between 160 and 400 m/s. One particular preferred embodiment consists in using a treatment composition based on eugenol and/or isoeugenol.

24 Claims, No Drawings

FOG TREATMENT METHOD USING A LIQUID COMPOSITION FOR TREATING FRUITS AND VEGETABLES AND IMPLEMENTING DEVICE

This application is a National Stage Filing of PCT/FR99/03006 filed Dec. 3, 1999.

The present invention relates to a thermal fogging process which is particularly appropriate for the thermal fogging of a liquid treatment composition over fruit and vegetables.

The thermal fogging of liquids over fruit and vegetables stored in closed spaces is now widespread in the art.

A thermal fogging device and the corresponding thermal fogging process are disclosed in particular in FR 84 10 372. This process is more specifically indicated for the thermal fogging of aqueous compositions. Although it results in the formation of a fine mist (at least 90% of the droplets formed have a diameter of less than or equal to 3 μm), the stability of this mist is not optimal. In fact, the droplets formed have a tendency to rapidly agglomerate to form large drops at the outlet of the thermal fogging device, so that the resulting coating on the fruit and vegetables is not the most even. Furthermore, according to this process of the prior art, the thickness of the coating depends on the duration of the thermal fogging.

These two characteristics render the use of the process of the prior art not very desirable in the case of the treatment of fruit and vegetables.

This is because, as the treated fruit and vegetables are intended for consumption, it is essential for a minimum of residue to remain present on their surfaces after treatment.

A thick coating of the fruit and vegetables is therefore to be avoided.

The process of the invention, by providing a thin and homogeneous coating of the fruit and vegetables and good stability of the mist formed, makes it possible to solve this problem.

The thermal fogging mist produced at the outlet of the thermal fogging device is conventionally composed of droplets exhibiting a temperature of between 150 and 200° C. which are driven with a linear velocity of at most 100 m/s. This mist is usually obtained from an aqueous liquid composition.

The inventors have discovered, surprisingly, that the stability of a thermal fogging mist composed of droplets exhibiting a temperature of greater than 200° C. which are driven with a linear velocity of greater than 110 m/s is greatly increased.

Without wishing to be restricted to any theory, it seems that, under these operating conditions, each droplet has a high electrostatic charge which would make it possible to avoid the agglomeration of the droplets with one another, while providing a monolayer and therefore particularly thin and homogeneous coating of the fruit and vegetables treated, due to electrical repulsion phenomena.

Thus, the invention relates more specifically to a process for the thermal fogging of a liquid composition for the treatment of fruit and vegetables, characterized in that a thermal fogging mist is produced composed of droplets exhibiting a temperature of 200 to 280° C. which are driven with a linear velocity of between 110 and 140 m/s.

It should be noted that the state of the art does not in any way teach that any improvement in the coating characteristics might result from an adjustment of these two parameters in the ranges indicated above. In point of fact, the values usually attributed to these two parameters do not fall in these specific ranges.

In a particularly advantageous way, the temperature of the droplets of the thermal fogging mist is between 210 and 280° C., preferably between 220° C. and 260° C.

In addition, it is preferable for the linear velocity of the droplets to be between 115 and 135 m/s and better still between 120 and 130 m/s.

Usually, in conventional thermal fogging devices, the thermal fogging mist is produced at the outlet of a cylindrical channel by injection, at the inlet of the said channel, of the treating liquid composition into a hot air jet projected at high speed into the said cylindrical channel via the said inlet.

According to a preferred embodiment of the invention, the temperature and velocity characteristics of the thermal fogging mist are obtained in a novel way by use of a nonaqueous treating liquid composition, the temperature of the hot air jet, before injection of the said composition, being set in a highly specific range and the linear velocity of the hot air jet, before injection, being adjusted above 160 m/s.

More specifically, the thermal fogging process employed involves the injection of a nonaqueous treating liquid composition into a hot air jet exhibiting a temperature of between 550 and 750° C. which is driven with a linear velocity of 160 to 400 m/s.

These conditions differ from those recommended in the prior art. According to FR 84 10 372, the hot air is heated to a much lower temperature, generally of at most 500° C.

According to the same document, the velocity for projection of the hot air into the channel, before injection of the treating composition, is generally between 100 m/s and 300 m/s. However, the velocities usually employed in this type of technique hardly ever exceed values of 130 m/s.

The linear projection velocity, before injection, is preferably between 200 and 280 m/s and better still between 220 and 250 m/s.

Likewise, a temperature of the hot air, before injection, of between 600 and 700° C. is particularly desirable. Temperature conditions of 600 to 650° C. are ideal.

According to a preferred embodiment of the invention, the diameter of the cylindrical channel into which the hot air is projected is adjusted to a value of between 12 and 25 mm, preferably between 16 and 20 mm, more particularly between 15 and 18 mm. A particularly appropriate value is about 18 mm.

This parameter makes it possible to more easily adjust the projection velocity of the hot air in the desired range of between 160 and 400 m/s.

The injection of the treating liquid composition into the hot air jet results in a fall in the temperature.

Due to the use of a nonaqueous liquid treating composition, this fall in temperature makes possible the production of a thermal fogging mist which exhibits the desired characteristics and in particular a high temperature of between 200 and 280° C.

Preferred nonaqueous compositions comprise 15 to 100% by weight of an active substance and 0 to 80% by weight (preferably 0 to 60% by weight) of a light organic solvent exhibiting a boiling point of between 70 and 130° C.

The active substance has a protective activity and/or prolongs the storage of the fruit and vegetables. This active substance can exhibit an antioxidant effect, a sprouting-inhibiting effect and/or a bactericidal effect and/or fungicidal effect.

Examples of antioxidants are ethoxyquin, diphenylamine, vitamin E and butylhydroxyanisole.

Examples of sprouting inhibitors are isopropyl chlorophenylcarbamate and some terpenes, such as carvone.

Examples of fungicides are, for example, thiabendazole, iprodione, sec-butylamine and terpenes.

The active substance of the treating composition can comprise one or more of these substances or else one or more substances exhibiting, at the same time, sprouting-inhibiting and/or anti-oxidant and/or bactericidal and/or fungicidal properties.

It is particularly advantageous to use, as active substance, a compound selected from eugenol, isoeugenol, a eugenol salt which is acceptable in foodstuffs, an isoeugenol salt which is acceptable in foodstuffs and their mixtures. In particular, alkali metal salts, such as sodium salts, lithium salts and potassium salts, are particularly preferred salts.

It should be understood that the treating composition can comprise, in addition to the active principle of eugenol or isoeugenol type, another active principle which opposes the growth of bacteria and fungi and/or which inhibits the sprouting of potatoes and onions or which exhibits antioxidant properties.

The active substance is preferably eugenol or isoeugenol, more preferably still eugenol.

One of the particularly advantageous characteristics of the active substances of eugenol and isoeugenol type is the broad spectrum of activity which is associated with them.

These compounds are effective as bactericides, fungicides and inhibitors of the sprouting of tubers (for example potato tubers) and bulbs (for example onion bulbs).

The superiority of these substances with respect to other terpenes is furthermore displayed in the case of highly varied bacterial strains and in the case of highly diverse species of fungi.

Bacterial strains are, for example, *Erwinia carotovora* or *Escherichia coli*.

Mention may be made, as examples of species of fungi, of *Fusarium oxysporum, Geotrichum candidum, Gloeosporium fructigenum, Penicillium digitatum, Penicillium expansum* or *Phytophthora parasitica*.

The treating composition is preferably nonaqueous.

According to a preferred embodiment of the invention, the liquid treatment composition is composed of the active substance alone.

However, the invention is not intended to be limited to this specific embodiment.

Thus, the active substance generally represents 15 to 100% by weight of the treating composition, for example from 25 to 100%, more preferably from 50 to 100% by weight, better still from 80 to 100% by weight.

When the presence of a solvent is necessary or desirable, the latter is preferably a nonaqueous solvent generally present in the composition in a proportion of 0 to 60–80% by weight, for example of 1 to 50% by weight, preferably of 3 to 40% by weight, better still of 5 to 35% by weight.

When the treating composition comprises from 15 to 80% of active substance, the solvent is generally present in a proportion of 15 to 80% by weight, better still of 20 to 40% by weight, very preferably of 30 to 35% by weight.

The solvent is in particular a solvent with a low boiling point selected from aliphatic alcohols, alkyl esters of carboxylic acids and aliphatic ketones. Mention may be made, by way of example, of $C_1$–$C_5$ aliphatic alcohols, $C_3$–$C_{10}$ aliphatic ketones and $C_1$–$C_5$ alkyl esters of aliphatic $C_1$–$C_5$ carboxylic acids.

Mention may be made, as organic solvent, of ethyl alcohol, isopropyl alcohol, acetone, methyl ethyl ketone, ethyl acetate, propyl acetate, butyl acetate, ethyl propionate and ethyl butyrate.

Ethyl alcohol and butyl acetate are preferred in particular.

In some cases, it may be desirable to add up to 40% by weight of a nonionic surfactant to the nonaqueous treating composition. When the fruit and vegetables to be treated are particularly delicate, such as strawberries, peaches and raspberries, the use of such a surfactant will be avoided.

The surfactants which can be used according to the invention are the nonionic surfactants usually indicated for the treatment of fruit and vegetables.

Mention may thus be made of:

the condensation product of an aliphatic fatty alcohol, preferably a $C_8$–$C_{22}$ fatty alcohol, with a $C_2$–$C_3$ alkylene oxide. The $C_2$–$C_3$ alkylene oxide can be ethylene oxide, propylene oxide or else a mixture of ethylene oxide and of propylene oxide in any proportions. An example of such surfactants is the condensation product of lauryl alcohol (or n-dodecyl alcohol) with 30 mol of ethylene oxide;

the condensation product of an alkylphenol, in which the alkyl chain is a $C_8$–$C_{22}$ alkyl chain, with a $C_2$–$C_3$ alkylene oxide. Here again, the condensation products with ethylene oxide, propylene oxide or else a mixture of ethylene oxide and of propylene oxide in any proportions are equally advantageous. Mention may be made, by way of example of such surfactants, of the condensation product of n-nonylphenol with 10 mol of ethylene oxide;

the condensation product of a fatty acid, preferably a $C_8$–$C_{22}$ fatty acid, with a $C_2$–$C_3$ alkylene oxide, for example ethylene oxide or propylene oxide or a mixture of ethylene oxide and of propylene oxide in any proportions. These condensation products have an alkoxylated chain on the hydroxyl functional group of the carboxyl group. Preferred surfactants of this group are the condensation products obtained from oleic acid, palmitic acid and stearic acid;

the condensation product of a $C_8$–$C_{22}$ fatty acid glyceride with a $C_2$–$C_3$ alkylene oxide, such as ethylene oxide and/or propylene oxide. Ethoxylated glyceryl palmitate is preferred among these;

the condensation product of a $C_8$–$C_{22}$ fatty acid ester of sorbitol with a $C_2$–$C_3$ alkylene oxide which can be ethylene oxide, propylene oxide or their mixtures. These compounds are polysorbates. A preferred example is sold under the name Tween 80.

The surfactant used according to the invention can comprise one or more of the surfactants listed above.

The content of nonionic surfactant will preferably remain between 3 and 15% by weight.

→Thus, the treating composition is generally a nonaqueous composition essentially comprising:

from 15 to 100% by weight of active principle;

from 0 to 80% by weight of an organic solvent with a low boiling point as defined above;

from 0 to 15% by weight of a nonionic surfactant.

More preferably still, the treating composition is a nonaqueous composition essentially comprising:

from 80 to 100% by weight of active principle;

from 0 to 10% by weight of nonionic surfactant;

from 0 to 10% by weight of solvent.

The inventors have found, surprisingly, that the use of a nonaqueous treating composition, in combination with the choice of a temperature of the hot air jet, before injection, of 550° C. to 750° C. and of a linear velocity of the hot air jet, before injection, of 160 to 400 m/s, under conditions such that the thermal fogging mist produced exhibits the desired temperature and velocity characteristics, results in the formation of droplets with a very low mean diameter of between 0.05 and 1 μm, generally between 0.3 and 0.8 μm.

This result confirms the advantage of the process of the invention with respect to conventional processes for the formation of thermal fogging mist.

This is because, conventionally, the size of the droplets formed is at least five times greater.

→In an alternative form, the treating composition, which can comprise water, essentially comprises:

from 15 to 80% by weight (preferably from 25 to 60%) of an active principle selected from eugenol, a eugenol salt .which is acceptable in foodstuffs, isoeugenol, an isoeugenol salt which is acceptable in foodstuffs and their mixtures;

from 0 to 10% by weight of one or more agents for reducing evaporation (preferably from 1 to 8%);

from 10 to 85% by weight (preferably from 25 to 60%) of a nonionic surfactant as defined above;

from 0 to 80% by weight (preferably from 0 to 30% by weight) of a solvent selected from water, alkanols, glycols, alkyl esters of alkanoic acids and their mixtures.

Examples of agents for reducing evaporation are polyterpenes which are dispersible in water; glycerol esters of pine resin; lacs; lecithins; drying oils; polyvinyl alcohol; polyvinylpyrrolidone; alkali metal polyacrylates; and gum arabic.

Isoprene polymers and natural rubber are polyterpenes which can be used in the context of the invention.

The glycerol esters of pine resin are abietic acid esters.

The lacs can be used as such or in a purified form, such as shellac resin.

The lecithins are mixtures of combinations of esters of oleic, stearic and palmitic acids with glycerophosphoric acid and choline.

Polyvinyl alcohol, polyvinylpyrrolidone, alkali metal polyacrylates and gum arabic are water-soluble synthetic resins which also function as agent for reducing evaporation of the active principle.

It must, however, be understood that the invention is not under any circumstances limited to the use of these specific water-soluble resins but that any other type of water-soluble resin might also be suitable provided that it is capable of reducing the evaporation of the active principle.

Preferred examples of drying oils are glyceryl linoleate, linoleic acid and linolenic acid.

The preferred alkanols are $C_1$–$C_2$ aliphatic alcohols.

The glycols denote, in the context of the invention, alkylene glycols and polyalkylene glycols.

The term "alkylene glycol" is understood to mean the dihydroxylated alcohols derived from aliphatic hydrocarbons by replacement of two hydrogen atoms with two hydroxyl groups. ($C_2$–$C_6$) Alkylene glycols, such as ethylene glycol and propylene glycol, are preferred.

The term "polyalkylene glycol" is understood to mean the compounds of formula:

$$HO—(C_pH_{2p}O)_n—H$$

where p and n are integers between 2 and 6.

Mention may be made, by way of example, of dipropylene glycol.

According to the invention, the $C_pH_{2p}O$ group is linear or branched. The preferred polyalkylene glycol according to the invention is dipropylene glycol.

The preferred alkyl esters of carboxylic acids are preferably the $C_1$–$C_6$ alkyl esters of ($C_1$–$C_6$) alkanoic acids, such as butyl acetate.

The treating composition is prepared in a way conventional in itself by simple mixing of its constituents.

When the treating composition comprises a salt which is acceptable in foodstuffs, the latter can be introduced into the composition, during its preparation, in the form of a salt or else in the neutral form; in the latter case, the salt is formed in situ by addition of an appropriate base to the composition.

The amount of treating composition which has to be applied to the fruit and vegetables depends on the nature of the fruit and vegetables concerned and on the method of application selected.

A total of 50 to 250 g of active principle per tonne of fruit or vegetables treated will be applied over a period of approximately six months by thermal fogging.

The treatment of the fruit and vegetables is generally carried out immediately after harvesting or during the retention of the fruit and vegetables during their storage in a cold room.

The thermal fogging can be continuous or intermittent during the storage period.

When the thermal fogging is carried out repeatedly in the storage space, the treatment is advantageously repeated every 7 to 40 days, preferably 15 to 30 days.

The invention relates more particularly to a thermal fogging process which makes it possible to inhibit the sprouting of bulbs (for example onion bulbs) and tubers (for example potato tubers) using a treating composition based on an active substance selected from eugenol, a eugenol salt which is acceptable in foodstuffs, isoeugenol, an isoeugenol salt which is acceptable in foodstuffs and their mixtures.

Furthermore, the invention relates to a thermal fogging process with a bactericidal and/or fungicidal effect using a treating composition based on an active substance selected from eugenol, a eugenol salt which is acceptable in foodstuffs, isoeugenol, an isoeugenol salt which is acceptable in foodstuffs and their mixtures.

According to another of its aspects, the invention relates to a device for implementing the process of the invention.

This device comprises a high-pressure electric ventilator which sends air into a first pipe equipped internally with an electrical element capable of heating the air to a temperature of 550 to 750° C., this pipe narrowing beyond the electrical element and emerging in a cylindrical channel with a smaller diameter in which the heated air has a linear velocity of between 160 and 400 m/s, and a pump which withdraws a liquid and injects it into the said cylindrical channel at the inlet of the latter.

In order to provide a linear velocity of the hot air of between, 160 and 400 m/s (preferably between 200 and 280 m/s) at the inlet of the cylindrical channel, the thermal fogging device is equipped with a powerful ventilator, the pressure of which varies between $0.20 \times 10^5$ Pa and $0.30 \times 10^5$ Pa, preferably between $0.22 \times 10^5$ Pa and $0.30 \times 10^5$ Pa, and the throughput of which varies between 30 and 80 $Sm^3/h$, more preferably between 55 and 70 $Sm^3/h$.

In order to adjust the linear velocity in the desired range, a person skilled in the art can also vary the diameter of the cylindrical channel. The latter is preferably between 12 and 25 mm, better still between 16 and 20 mm, more particularly between 15 and 18 mm.

By virtue of the use of an electric ventilator which gives a constant air throughput in the pipes of the device, of an electrical element which gives a constant heat and of a positive displacement pump which gives an absolutely constant throughput of liquid, it is possible to obtain a thermal fogging which is very consistent and consequently good consistency in the size of the particles.

The electrical element is preferably capable of heating the air to a temperature of 600 to 700° C. and better still of 600 to 650° C.

The electrical power of the electrical element is preferably between 5 and 20 kW, better still between 5 and 8 kW, for example 10 kW or 7.5 kW.

According to the process of the invention, the thermal fogging mist produced at the outlet is composed of droplets exhibiting a temperature of between 200 and 280° C. which are driven with a linear velocity of between 110 and 140 m/s.

In order to satisfy these conditions, a person skilled in the art will easily determine:
- the length of the cylindrical channel,
- the throughput and the temperature of the treating composition, during its injection at the inlet of the said cylindrical channel, in view of the temperature of the hot air jet and of its linear velocity before injection.

A length of the cylindrical channel of between 300 and 1500 mm is generally suitable.

Likewise, the throughput for injection of the liquid composition is generally set at between 5 and 30 l/h, preferably between 10 and 25 l/h, for example between 13 and 20 l/h.

As regards the temperature of the liquid composition, the latter is generally between 10 and 30° C., preferably between 15 and 25° C., for example between 20 and 25° C.

According to an alternative form, it is possible to separate off the ventilation part with respect to the heating and liquid injection part and thus to create a centralized stationary ventilation plant which can serve several fogging points.

The invention will be set out below in more detail with reference to the appended drawing, in which:
- the single Figure is a diagrammatic cross sectional view of a device according to the invention.

The device represented in the single Figure comprises a blower 1 supplying a pressure of 25,000 Pa and a throughput of 60 Sm$^3$/h.

The blower 1 sends air into a pipe 2, inside which is positioned an electrical element 3. The pipe extends beyond the element 3 via a combining tube 4 which emerges in a pipe 5 with a diameter of 18 mm and a length of 800 mm.

The shaft 6 of the ventilator 1 is driven by an electric motor (not represented). The shaft 6 also drives a positive displacement pump 7, for example via a belt 8 or alternatively directly.

The pump 7 withdraws, via a pipe 9, the liquid 10 present in a tank 11 and injects it at the inlet of the pipe 5 via a pipe 12. A three-way valve 13, mounted on this pipe 12, makes it possible for the liquid to return to the tank 11 via a pipe 14 during a start-up phase.

In the following examples, the thermal fogging device used is that in the appended figure, in which:
- the diameter of the cylindrical channel is 18 mm;
- the length of the cylindrical channel is 800 mm;
- the electrical power of the electrical element is 10 kW;
- the temperature of the heated air at the outlet of the element is approximately 625° C.;
- the linear projection velocity of the hot air, before injection, is 220 m/s;
- the air throughput of the ventilator is 60 Sm$^3$/h;
- the pressure of the ventilator is 25,000 Pa.

EXAMPLE 1

The following composition, comprising, as percentage by weight:
- 60% of active material;
- 7% of a polysorbate (Tween 80, sold by the Company ICI);
- 33% of butyl acetate, is prepared in a conventional way.

This composition is injected into the cylindrical channel via the pipe 12 of the device represented in the Figure at a throughput of 15 l/h, the temperature of the composition being 20–25° C.

A thermal fogging mist is thus obtained with a mean diameter for the droplets of 0.4 μm. The linear velocity of the mist droplets at the outlet of the cylindrical channel is 125 m/s and the temperature of the droplets is 240° C.

EXAMPLE 2

The composition injected into the thermal fogging device contains 100% of eugenol. The conditions for injection of the composition are the same as in Example 1. The characteristics of the thermal fogging mist are the same as in Example 1.

EXAMPLE 3

The procedure is as in Example 1, starting from a treating liquid composition comprising:
- 90% by weight of active material;
- 10% by weight of Tween 80.

The characteristics of the thermal fogging mist are the same as in Example 1. The conditions for injection of the composition are the same as in Example 1.

EXAMPLE 4

The fungicidal activity of eugenol and of isoeugenol was demonstrated in vitro and compared with that of other terpenes.

The Cristomalt medium used for the evaluations of the fungicidal activities comprises 0.1% of Cristomalt (malt extract) and 0.2% of agar.

This culture medium is, after sterilization, brought to 55° C. The terpene compound tested is then introduced in the pure form into the culture medium under warm conditions. Immediately after agitating, the medium, enriched with the terpene product, is poured into Petri dishes (diameter 9 cm, filled with 20 ml of medium). The agar-comprising medium solidifies on cooling. The Petri dishes are then inoculated with plugs, with a diameter of 6 mm, withdrawn from the edge of a culture of the tested fungus, which culture is obtained on Cristomalt medium.

Inoculation is carried out at 22° C.

The mycelial growth was determined periodically (5 to 15 days, according to the species of fungus).

The results are expressed in Table 3 below in terms of MIC, which is the content (in μg/ml) which makes it possible to obtain complete inhibition of mycelial growth.

It should be noted that ranges in variation of the MIC values are shown in Table 1. In f act, each experiment was carried out several times, so that, for each terpene and for each species of fungus, a minimum value and a maximum value were obtained.

TABLE 1

|    | CARVONE | EUCALYPTOL | EUGENOL | ISO-EUGENOL | TERPINEOL | SAFROLE |
|----|---------|------------|---------|-------------|-----------|---------|
| AA | 40–80   | >1280      | 20–40   | 20–40       | 40–80     | 80–160  |
| BC | 20–40   | 640–1280   | 20–40   | 20–40       | 40–80     | 80–160  |
| FO | 40–80   | 640–1280   | 20–40   | 20–40       | 40–80     | 80–160  |
| GC | 80–160  | 320–640    | 10–20   | 10–20       | 80–160    | 160–230 |
| GR | 40–80   | 320–640    | 20–40   | 20–40       | 40–80     | 40–80   |
| PD | 40–80   | >1280      | 20–40   | 20–40       | 40–80     | 160–230 |
| PE | 80–160  | >1280      | 20–40   | 20–40       | 40–80     | 640–1280|
| PV | 80–160  | 160–320    | 40–80   | 20–40       | 40–80     | 80–160  |
| PhP| 40–80   | 320–640    | 20–40   | 20–40       | 20–40     | 40–80   |

Throughout the text of the present description, the meanings of the abbreviations used in Table 3 are as follows:
AA *Alternaria alternata*
BC *Botrytis cinerea*
FO *Fusarium oxysporum*
GC *Geocrichum candidum*
GR *Gliocladium roseum*
PD *Penicillium digitatum*
PE *Penicillium expansum*
PV *Phlyctaena vagabonda* ("Gloeosporium")
PhP *Phytophtora parasitica*

The results obtained are analysed simply by using the assessment scale illustrated in Table 2:

TABLE 2

| MIC within the range delimited by the two values shown in ppm (μg/ml) | Inhibition grades |
|---|---|
| 10–20   | 8 (Strong inhibition) |
| 20–40   | 7 |
| 40–80   | 6 |
| 80–160  | 5 |
| 160–320 | 4 |
| 320–640 | 3 |
| 640–1280| 2 |
| >1280   | 1 (Weak inhibition) |

The results obtained have been expressed in Table 3 using the scale in Table 2.

TABLE 3

|    | CAR-VONE | EUCA-LYP-TOL | EU-GENOL | ISO-EU-GENOL | TERP-INEOL | SA-FROLE |
|----|------|------|------|------|------|------|
| AA | 6 | 1 | 7 | 7 | 6 | 5 |
| BC | 7 | 2 | 7 | 7 | 6 | 5 |
| OF | 6 | 2 | 7 | 7 | 6 | 5 |
| GC | 5 | 3 | 8 | 8 | 5 | 4 |
| GR | 6 | 3 | 7 | 7 | 6 | 6 |
| PD | 6 | 1 | 7 | 7 | 6 | 4 |
| PE | 5 | 1 | 7 | 7 | 6 | 2 |
| PV | 5 | 4 | 6 | 7 | 6 | 5 |
| PhP| 6 | 3 | 7 | 7 | 7 | 6 |
| Total of the degrees of inhibition | 52 | 20 | 63 | 64 | 54 | 42 |

It clearly emerges from Table 3 that eugenol and isoeugenol are markedly more active than the other terpenes.

EXAMPLE 5

The activity of eugenol and of isoeugenol on the germination of the spores was evaluated in vitro and compared with that of other terpenes.

The procedure of Example 4 is used to do this, except that the concentration of eugenol and of isoeugenol was set at x μg/ml in the culture media used and that 50 μl of a suspension of spores, adjusted to 100,000 spores/ml, are deposited in each Petri dish.

The same experiment was carried out starting with a terpene-free culture medium (control test).

The results were evaluated using the following assessment criteria:

++: germination of the spores comparable with that of the control

+: considerable reduction in the level of spores germinated

0: spores not germinated

The results obtained for 3 different concentrations of terpenes in the culture medium, namely 40 μg/ml, 80 μg/ml and 1280 μg/ml, are listed in Tables 4, 5 and 6.

TABLE 4

(x = 40 μg/ml)

|    | CAR-VONE | EUCA-LYP-TOL | EU-GENOL | ISO-EU-GENOL | TERP-INEOL | SA-FROLE |
|----|----|----|----|----|----|----|
| AA | + | ++ | 0 | 0  | ++ | ++ |
| BC | + | ++ | 0 | ++ | +  | +  |
| FO | + | ++ | 0 | 0  | ++ | ++ |
| GC | + | ++ | 0 | 0  | ++ | ++ |
| PD | + | +  | 0 | 0  | ++ | +  |
| PE | + | +  | 0 | 0  | ++ | +  |
| PV | + | ++ | 0 | 0  | ++ | +  |
| PhP| 0 | ++ | 0 | 0  | +  | 0  |

TABLE 5

(x = 80 μg/ml)

|    | CAR-VONE | EUCA-LYP-TOL | EU-GENOL | ISO-EU-GENOL | TERP-INEOL | SA-FROLE |
|----|----|----|----|----|----|----|
| AA | 0 | ++ | 0 | 0 | 0 | + |
| BC | 0 | ++ | 0 | 0 | 0 | 0 |
| FO | 0 | ++ | 0 | 0 | 0 | + |
| GC | 0 | +  | 0 | 0 | + | + |
| PD | 0 | +  | 0 | 0 | 0 | + |
| PE | 0 | +  | 0 | 0 | + | + |
| PV | 0 | +  | 0 | 0 | 0 | + |
| PhP| 0 | +  | 0 | 0 | 0 | 0 |

TABLE 6

(x = 1280 µg/ml)

|  | CAR-VONE | EUCA-LYP-TOL | EU-GENOL | ISO-EU-GENOL | TERP-INEOL | SA-FROLE |
|---|---|---|---|---|---|---|
| AA | 0 | 0 | 0 | 0 | 0 | 0 |
| BC | 0 | 0 | 0 | 0 | 0 | 0 |
| FO | 0 | 0 | 0 | 0 | 0 | 0 |
| GC | 0 | 0 | 0 | 0 | 0 | 0 |
| PD | 0 | + | 0 | 0 | 0 | 0 |
| PE | 0 | + | 0 | 0 | 0 | + |
| PV | 0 | 0 | 0 | 0 | 0 | 0 |
| PhP | 0 | 0 | 0 | 0 | 0 | 0 |

It clearly results from these various tables that eugenol and isoeugenol exhibit a much higher activity than that of the other terpenes. A concentration of 40 µg/ml is sufficient to inhibit the germination of the spores.

EXAMPLE 6

The bactericidal activity of eugenol and isoeugenol was evaluated in vitro and compared with that of other terpenes.

The culture medium used is the following LB medium:
Bactotryptone: 1% by weight
Yeast extract: 0.5% by weight
NaCl: 0.5% by weight
Agar: 1.2% by weight.

A suspension of bacteria at $10^6$ CFU/ml was prepared in sterilized water from the LB medium. 200 µl of this bacterial suspension were added to 20 ml of presterilized LB culture medium brought to 55° C. The tested terpene is then added to the culture medium. After agitation, the medium is immediately divided among Petri dishes. The medium solidifies on cooling.

Incubation is carried out at 28° C. when the bacterium is *Erwinia carotovora* and at 37° C. when the bacterium is *Escherichia coli*.

The growth of mould in the culture medium is observed. The same experiment is carried out in the absence of terpene (control experiment).

The results are evaluated using the following assessment scale:
++: mould growth identical to the control
+: mould present with a marked reduction in growth with respect to the control
: complete absence of growth.

The results obtained for 3 different concentrations, namely 20, 80 and 320 µg/ml, in the case of the bacterium *Erwinia carotovora* are summarized in Table 7.

TABLE 7

| Concentration in µg/ml | CAR-VONE | EUCA-LYP-TOL | EU-GENOL | ISO-EU-GENOL | TERP-INEOL | SA-FROLE |
|---|---|---|---|---|---|---|
| 20 | ++ | ++ | + | + | ++ | ++ |
| 80 | + | ++ | – | – | + | ++ |
| 320 | – | ++ | – | – | – | + |

In another series of experiments, the concentration of terpene needed to completely inhibit the growth of the bacteria (MIC) was determined. The protocol used is that described above. The results obtained are listed in Table 8 below.

TABLE 8

| MIC in µg/ml | CAR-VONE | EUCA-LYP-TOL | EU-GENOL | ISO-EU-GENOL | TERP-INEOL | SA-FROLE |
|---|---|---|---|---|---|---|
| Erwinia sp. | 80–160 | 320–640 | 20–40 | 20–40 | 80–160 | 320–640 |
| Escherichia sp. | 320–640 | >640 | 40–80 | 40–80 | 160–320 | >640 |

Eugenol and isoeugenol prove to be the most active with respect to both bacteria.

EXAMPLE 7

The effectiveness of eugenol and of isoeugenol in the sprouting-inhibiting treatment of potato tubers was evaluated and compared with that of other terpenes.

The following compositions were used in the case of eucalyptol, eugenol, isoeugenol, limonene, safrole and terpineol:
60% by weight of terpene;
7% by weight of a nonionic emulsifier;
33% by weight of butyl acetate.

In the case of L-carvone, the following composition was employed:
30% by weight of L-carvone;
10% by weight of ethanol;
5% by weight of nonionic emulsifier;
20% by weight of water;
35% by weight of propylene glycol.

Isopropyl chlorophenylcarbamate (CIPC) is a compound used in the art as sprouting inhibitor for potato tubers. Its activity was compared with that of eugenol and of isoeugenol.

The composition based on isopropyl chlorophenylcarbamate has the following formulation:
20% by weight of isopropyl chlorophenyl-carbamate;
50% by weight of propylene glycol;
10% by weight of nonionic emulsifier;
20% of water.

Each of the compositions tested was applied by thermal fogging. The temperature at the outlet of the thermal fogging device was 240° C., except in the case of the compositions based on L-carvone and on CIPC, where it was 180° C.

The amount of composition which has to be applied is calculated in each case so as to obtain an equivalent concentration of active material on the potato tubers.

In this example, repeated applications were carried out by following the following protocol:
45 g/tonne of tubers at the beginning of storage;
15 g/tonne of tubers every 20 days; so that, after 6 months, 165 g of active principle have been applied per tonne of tubers.

During storage, the tubers were stored in a cold room at a temperature of 8 to 9° C.

The results obtained after 5 months are listed in Table 9.

TABLE 9

| PRODUCTS | Loss in weight of the tubers (%) | Unsprouted tubers (%) | Tubers at the white point stage (%) | Tubers with sprouts <2 mm (%) | Tubers with sprouts 2 to 5 mm (%) | Tubers with sprouts >5 mm (%) | Tubers with sprouts >2 mm (%) | Total weight of the sprouts >2 mm (g) |
|---|---|---|---|---|---|---|---|---|
| EUCALYPTOL | 3.2 | 4.4 | 10.2 | 26.7 | 36.3 | 22.4 | 58.4 | 46.2 |
| SAFROLE | 3.6 | 1.2 | 6.6 | 15.6 | 40.1 | 36.5 | 76.6 | 57.0 |
| LIMONENE | 4.5 | 0.5 | 1.2 | 1.5 | 8.7 | 88.1 | 96.8 | 283.8 |
| EUGENOL | 2.6 | 7.5 | 45.3 | 35.2 | 6.2 | 5.8 | 12.0 | 3.6 |
| ISOEUGENOL | 2.7 | 6.2 | 22.6 | 56.8 | 10.6 | 3.8 | 14.4 | 8.5 |
| L-CARVONE | 3.3 | 4.0 | 8.7 | 32.3 | 28.8 | 26.2 | 55.0 | 42.0 |
| TERPINEOL | 3.8 | 4.8 | 2.4 | 22.2 | 46.1 | 24.5 | 70.6 | 55.3 |
| CIPC | 4.1 | 1.2 | 81.7 | 3.7 | 2.3 | 15.7 | 18 | 14.8 |
| CONTROL | 5.4 | 0.0 | 0.0 | 0.0 | 0.0 | 100 | 100 | 436.3 |

It clearly results from Table 9 that:
the maximum percentages of unsprouted tubers are obtained in the case of eugenol and of isoeugenol;
eugenol and isoeugenol are the two terpenes which have resulted in a very low percentage of sprouts with a size of greater than 2 mm.
The superiority of eugenol and of isoeugenol therefore cannot be disputed.

What is claimed is:

1. Process for the thermal fogging of a non-aqueous liquid composition for the treatment of fruit and vegetables, using a liquid treatment composition which comprises:

from 80 to 100% by weight of an active principle selected from the group consisting of eugenol, an eugenol salt which is acceptable in foodstuffs, isoeugenol, an isoeugenol salt which is acceptable in foodstuffs and their mixtures;

from 0% to 10% by weight of non-ionic surfactant; and from 0 to 10% by weight of solvent, wherein a thermal fogging mist is produced, from the composition, composed of droplets exhibiting a temperature of 200 to 280° C. which are driven with a linear velocity of between 110 and 140 m/s.

2. Process according to claim 1, wherein the temperature of the droplets of the thermal fogging mist is between 220° and 260° C.

3. Process according to claim 1 or 2, wherein the linear velocity of the droplets of the thermal fogging mist is between 115 and 135 m/s.

4. Process according to claim 3, wherein the linear velocity of the droplets is between 120 and 130 m/s.

5. Process according to claim 1 or 2, comprising the formation of the thermal fogging mist at the outlet of a cylindrical channel by injection, at the inlet of the channel, of the composition into a hot air jet projected at high speed into the cylindrical channel via the inlet, wherein the hot air jet exhibits, before injection, a temperature of between 550° and 750° C. and is driven, before injection, with a linear velocity of 160 to 400 m/s.

6. Process according to claim 3, comprising the formation of the thermal fogging mist at the outlet of a cylindrical channel by injection, at the inlet of the channel, of the composition into a hot air jet projected at high speed into the cylindrical channel via the inlet, wherein the hot air jet exhibits, before injection, a temperature of between 550° and 750° C. and is driven, before injection, with a linear velocity of 160 to 400 m/s.

7. Process according to claim 5, wherein the linear velocity before injection is between 200 and 280 m/s.

8. Process according to claim 6, wherein the linear velocity before injection is between 200 and 280 m/s.

9. Process according to claim 5, wherein the temperature of the hot air jet, before injection, is between 600° and 700° C.

10. Process according to claim 6, wherein the temperature of the hot air jet, before injection, is between 600° and 700° C.

11. Process according to claim 7, wherein the temperature of the hot air jet, before injection, is between 600° and 700° C.

12. Process according to claim 8, wherein the temperature of the hot air jet, before injection, is between 600° and 700° C.

13. Process according to claim 5, wherein the diameter of the channel is between 12 and 25 mm.

14. Process according to claim 13, wherein the diameter of the channel is between 16 and 20 mm.

15. Process according to claim 6, wherein the diameter of the channel is between 12 and 25 mm.

16. Process according to claim 9, wherein the diameter of the channel is between 12 and 25 mm.

17. Process according to claim 10, wherein the diameter of the channel is between 12 and 25 mm.

18. Process according to claim 11, wherein the diameter of the channel is between 12 and 25 mm.

19. Process according to claim 12, wherein the diameter of the channel is between 12 and 25 mm.

20. Process according to claim 1, wherein the organic solvent is selected from the group consisting of an aliphatic alcohol, an aliphatic ketone and an alkyl ester of an aliphatic carboxylic acid.

21. Process according to claim 20, wherein the solvent is ethyl alcohol or butyl acetate.

22. Process according to claim 1, wherein the active principle is eugenol.

23. Process according to claim 1, for the sprouting-inhibiting treatment of bulbs and tubers.

24. Process according to claim 1, for bactericidal and/or fungicidal treatment.

* * * * *